US010360912B1

(12) United States Patent
Jones et al.

(10) Patent No.: US 10,360,912 B1
(45) Date of Patent: Jul. 23, 2019

(54) PRESENTATION OF INDICATIONS WITH RESPECT TO QUESTIONS OF A COMMUNICATION SESSION (71) Applicant: Sorenson IP Holdings, LLC, Salt Lake City, UT (US)

(72) Inventors: Michael Jones, Farmington, UT (US); Jeff Smith, Herriman, UT (US); Adam Montero, Midvale, UT (US)

(73) Assignee: Sorenson IP Holdings, LLC, Salt Lake City, UT (US)

( * ) Notice: Subject to any disclaimer, the term of this patent is extended or adjusted under 35 U.S.C. 154(b) by 0 days.

(21) Appl. No.: 15/967,298

(22) Filed: Apr. 30, 2018

(51) Int. Cl.
*G10L 15/26* (2006.01)
*G10L 15/22* (2006.01)
*G06F 3/0484* (2013.01)
*G16H 80/00* (2018.01)
*H04M 3/42* (2006.01)
(Continued)

(52) U.S. Cl.
CPC .......... *G10L 15/265* (2013.01); *G06F 3/0484* (2013.01); *G10L 15/22* (2013.01); *G16H 80/00* (2018.01); *G06F 17/271* (2013.01); *G06F 17/2775* (2013.01); *G06F 17/2785* (2013.01); *G10L 15/1822* (2013.01); *H04M 3/42068* (2013.01); *H04M 3/42221* (2013.01); *H04M 2201/60* (2013.01)

(58) Field of Classification Search
CPC .............. G06F 17/271; G06F 17/2775; G06F 17/2785; G06F 17/2755; G10L 15/265; G10L 15/1822
See application file for complete search history.

(56) References Cited

U.S. PATENT DOCUMENTS 5,369,704 A   11/1994   Bennett et al.
6,823,054 B1 *  11/2004   Suhm ...................... H04M 3/36
                                                                     379/112.01
(Continued)

FOREIGN PATENT DOCUMENTS

CN    104269171 A    1/2015
KR    20140123370 A    10/2014

OTHER PUBLICATIONS

DialogTech Voice-To-Text Transcription Gives Users a Choice, website: https://www.dialogtech.com/press_releases/ifbyphone-voice-to-text-transcription-gives-users-a-choice, published on Apr. 13, 2010.
(Continued)

*Primary Examiner* — Eric Yen
(74) *Attorney, Agent, or Firm* — Maschoff Brennan (57) ABSTRACT

According to one or more embodiments of the present disclosure, operations regarding providing indications with respect to questions of a communication session may include obtaining transcript data. The transcript data may include a transcription of audio of the communication session. The operations may further include obtaining multiple questions determined to be asked during the communication session. The operations may further include determining, based on an analysis of the transcript data during the communication session, which of the questions have been asked during the communication session. In addition, the operations may include causing, during the communication session, the device involved in the communication session to indicate which of the questions have been asked.

20 Claims, 3 Drawing Sheets

(51) Int. Cl.
 *G10L 15/18* (2013.01)
 *G06F 17/27* (2006.01)

(56) References Cited

U.S. PATENT DOCUMENTS

| | | | |
|---|---|---|---|
| 8,811,593 B1 | 8/2014 | Morrissey | |
| 9,324,323 B1* | 4/2016 | Bikel | G10L 15/183 |
| 9,652,113 B1* | 5/2017 | Colson | H04L 12/1822 |
| 9,736,309 B1 | 8/2017 | Bentitou et al. | |
| 9,953,650 B1* | 4/2018 | Falevsky | G10L 15/22 |
| 10,235,998 B1* | 3/2019 | Khaleghi | G10L 15/22 |
| 2002/0010596 A1* | 1/2002 | Matory | G06Q 50/22 |
| | | | 705/2 |
| 2002/0078139 A1* | 6/2002 | Dutta | G09B 7/02 |
| | | | 709/203 |
| 2003/0033294 A1* | 2/2003 | Walker | G06Q 30/02 |
| 2008/0172245 A1 | 7/2008 | Imai et al. | |
| 2009/0119371 A1 | 5/2009 | Chang et al. | |
| 2010/0039296 A1* | 2/2010 | Marggraff | G06F 3/03545 |
| | | | 341/20 |
| 2011/0137138 A1* | 6/2011 | Johansson | G16H 10/20 |
| | | | 600/301 |
| 2014/0057240 A1 | 2/2014 | Colby et al. | |
| 2014/0307859 A1 | 10/2014 | Karimi-Cherkandi et al. | |
| 2015/0149177 A1* | 5/2015 | Kalns | G10L 15/1822 |
| | | | 704/257 |
| 2015/0339390 A1 | 11/2015 | Urdiales Delgado et al. | |
| 2016/0352902 A1* | 12/2016 | Raanani | G06Q 30/02 |
| 2017/0213190 A1* | 7/2017 | Hazan | G10L 25/63 |
| 2019/0116210 A1* | 4/2019 | Keen | H04L 65/403 |

OTHER PUBLICATIONS

Make Your Call Center More Efficient with Powerful Speech to Text, website: https://transcribeme.com/blog/call-center-speech-to-text, Dec. 29, 2016.

* cited by examiner

PRESENTATION OF INDICATIONS WITH RESPECT TO QUESTIONS OF A COMMUNICATION SESSION

FIELD

The embodiments discussed herein are related to presentation of indications with respect to questions of a communication session.

BACKGROUND

Communication sessions between persons (e.g., telephonic communication sessions, video communication sessions, etc.) may have questions associated therewith. For example, during a communication session between a healthcare professional and a patient, the healthcare professional may ask the patient certain questions. As another example, during a customer service communication session, a customer service representative may ask a customer certain questions.

The subject matter claimed herein is not limited to embodiments that solve any disadvantages or that operate only in environments such as those described above. Rather, this background is only provided to illustrate one example technology area where some embodiments described herein may be practiced.

SUMMARY

According to one or more embodiments of the present disclosure, operations regarding providing indications with respect to questions of a communication session may include obtaining transcript data. The transcript data may include a transcription of audio of the communication session. The operations may further include obtaining multiple questions determined to be asked during the communication session. The operations may further include determining, based on an analysis of the transcript data during the communication session, which of the questions have been asked during the communication session. In addition, the operations may include causing, during the communication session, the device involved in the communication session to indicate which of the questions have been asked.

The objects and advantages of the embodiments will be realized and achieved at least by the elements, features, and combinations particularly pointed out in the claims. Both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

In some instances, it may be desired that certain questions are asked and answered during a communication session. For instance, in some communication sessions between a healthcare professional and a patient, certain questions regarding the patient's health status and/or general condition may be asked by the healthcare professional to allow the healthcare professional to assess treatment of the patient or may be required to be asked in accordance with a policy. However, during the communication session, the healthcare professional may forget or not think to ask one or more questions that may be useful. Additionally or alternatively, the patient may forget to answer one or more of the questions that may be asked.

In some embodiments, a system may be configured to obtain one or more questions that may be determined to be asked during a communication session between multiple participants. In these or other embodiments, the system may be configured to determine which of the questions have been asked and/or answered during the communication session. For example, as detailed below, in some embodiments, the system may be configured to generate a transcription of what is said, e.g., verbally communicated, during the communication session. The system may use the transcription to identify which of the questions have been asked and/or answered. In these or other embodiments, the system may be configured to cause a device of a participant in the communication session to indicate, during the communication session, which of the questions have been asked and/or answered. The providing of the indication during the communication session may help ensure that certain information is communicated during the communication session rather than being overlooked or forgotten.

As discussed in detail below, one or more embodiments of the present disclosure regarding determining which of the questions have been asked and how the questions are indicated as asked enables a corresponding communication system to provide information regarding questions asked and/or answered. Therefore, according to one or more embodiments of the present disclosure, the technological field of communication systems may be improved by providing a technological mechanism of indicating questions that have been asked and/or answered that may improve the efficacy and/or efficiency of communication sessions.

Figure 1:
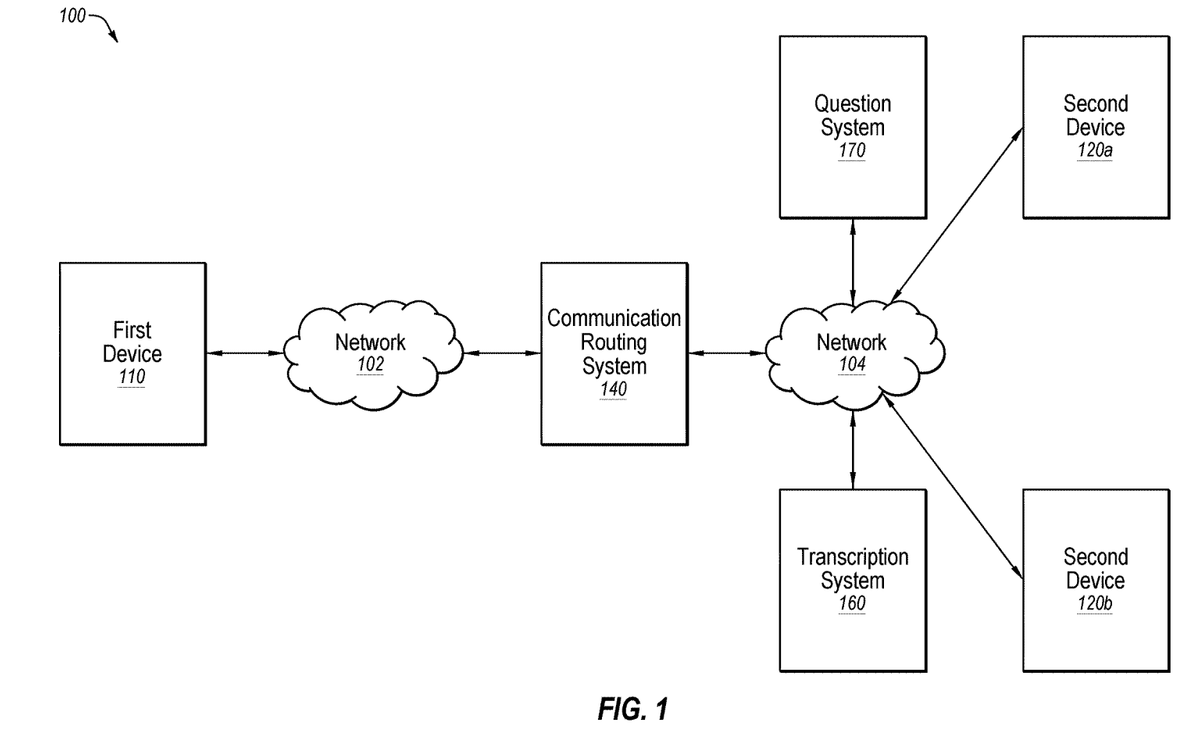
FIG. 1 illustrates an example environment related to providing indications with respect to questions of a communication session.

Turning to the figures, FIG. 1 illustrates an example environment 100 related to providing indications with respect to questions of a communication session. The environment 100 may be arranged in accordance with at least one embodiment described in the present disclosure. The environment 100 may include a first network 102; a second network 104; a first device 110; second devices 120, including a first second-device 120a and a second second-device 120b; a communication routing system 140; a transcription system 160; and a question system 170.

The first network 102 may be configured to communicatively couple the first device 110 and the communication routing system 140. The second network 104 may be configured to communicatively couple the second devices 120, the communication routing system 140, the transcription system 160, and the question system 170.

In some embodiments, the first and second networks 102 and 104 may each include any network or configuration of networks configured to send and receive communications between devices. In some embodiments, the first and second networks 102 and 104 may each include a conventional type network, a wired or wireless network, and may have numerous different configurations. Furthermore, the first and second networks 102 and 104 may each include a local area network (LAN), a wide area network (WAN) (e.g., the Internet), or other interconnected data paths across which multiple devices and/or entities may communicate.

In some embodiments, the first and second networks 102 and 104 may each include a peer-to-peer network. The first and second networks 102 and 104 may also each be coupled to or may include portions of a telecommunications network for sending data in a variety of different communication protocols. In some embodiments, the first and second networks 102 and 104 may each include Bluetooth® communication networks or cellular communication networks for sending and receiving communications and/or data. The first and second networks 102 and 104 may also each include a mobile data network that may include third-generation (3G), fourth-generation (4G), long-term evolution (LTE), long-term evolution advanced (LTE-A), Voice-over-LTE ("VoLTE") or any other mobile data network or combination of mobile data networks. Further, the first and second networks 102 and 104 may each include one or more IEEE 802.11 wireless networks. In some embodiments, the first and second networks 102 and 104 may be configured in a similar manner or a different manner. In some embodiments, the first and second networks 102 and 104 may share various portions of one or more networks. For example, each of the first and second networks 102 and 104 may include the Internet or some other network.

The first device 110 may be any electronic or digital device. For example, the first device 110 may include or may be included in a desktop computer, a laptop computer, a smartphone, a mobile phone, a tablet computer, a television set-top box, a smart television, or any other electronic device with a processor. In some embodiments, the first device 110 may include computer-readable-instructions stored on one or more computer-readable media that are configured to be executed by one or more processors in the first device 110 to perform operations described in this disclosure. The first device 110 may be configured to communicate with, receive data from, and direct data to, the communication routing system 140 and/or the second devices 120. During a communication session, audio, video, and/or a transcription of the audio may be presented by the first device 110.

In some embodiments, the first device 110 may be associated with a first user. The first device 110 may be associated with the first user based on the first device 110 being configured to be used by the first user. In these and other embodiments, the first user may be registered with the communication routing system 140 and the first device 110 may be listed in the registration of the first user. Alternatively or additionally, the first device 110 may be associated with the first user by the first user being the owner of the first device 110 and/or being controlled by the first user.

The second devices 120 may be any electronic or digital devices. For example, the second devices 120 may include, or may be included in, a desktop computer, a laptop computer, a smartphone, a mobile phone, a tablet computer, a television set-top box, a smart television, or any other electronic device with a processor. In some embodiments, the second devices 120 may each include, or be included in, the same, different, or combinations of electronic or digital devices. In some embodiments, the second devices 120 may each include computer-readable instructions stored on one or more computer-readable media that are configured to be executed by one or more processors in the second devices 120 to perform operations described in this disclosure.

The second devices 120 may each be configured to communicate, receive data from and direct data to, the communication routing system 140. Alternatively or additionally, each of the second devices 120 may be configured to, individually or in a group, participate in a communication session with the first device 110 through the communication routing system 140. In some embodiments, the second devices 120 may each be associated with a second user or be configured to be used by a second user. During a communication session, audio, video, and/or a transcription of the audio may be presented by the second devices 120 for the second users.

In some embodiments, the second users may be healthcare professionals. In these and other embodiments, healthcare professionals may be individuals with training or skills to render advice with respect to mental or physical health, including, nurses, nurse practitioners, medical assistants, doctors, physician assistants, counselors, psychiatrists, psychologists, or doulas, among other healthcare professionals. In these and other embodiments, the first user may be an individual in their home who has a healthcare need. For example, the first user may be an individual at home who is recovering from a surgery and who has a need for in-home care from a healthcare professional. Alternatively or additionally, the first user may be an individual at home who has an illness for which in-home care from a healthcare professional is preferable. Alternatively or additionally, the first user may be an individual at a care facility or some other facility.

In some embodiments, each of the communication routing system 140, the transcription system 160, and the question system 170 may include any configuration of hardware, such as processors, servers, and databases that are networked together and configured to perform one or more tasks. For example, each of the communication routing system 140, the transcription system 160, and the question system 170 may include multiple computing systems, such as multiple servers that each include memory and at least one processor, which are networked together and configured to perform operations as described in this disclosure, among other operations. In some embodiments, each of the communication routing system 140 the transcription system 160, and the question system 170 may include computer-readable instructions stored on one or more computer-readable media that are configured to be executed by one or more processors in each of the communication routing system 140, the transcription system 160, and the question system 170 to perform operations described in this disclosure. Additionally, in some embodiments, the communication routing system 140, the transcription system 160, and/or the question system 170 may be configured as a distributed system in which one or more of the operations associated therewith may be performed by separate components that may be remotely located away from each other and communicatively coupled (e.g., via a network such as the networks 102 and 104).

Generally, the communication routing system 140 may be configured to establish and manage communication sessions between the first device 110 and one or more of the second devices 120. The transcription system 160 may be configured to generate and provide transcriptions of audio from communication sessions established by the communication routing system 140. The question system 170 may also be configured to obtain one or more questions that may be determined to be asked during communication sessions, determine which of the questions may have been asked or answered during communication sessions, and cause the first device 110 and/or one or more of the second devices 120 to indicate, during the communication sessions, which of the questions have been asked or answered.

An example of the interaction of the elements illustrated in the environment 100 is now provided. As described below, the elements illustrated in the environment 100 may interact to establish a communication session between the first device 110 and one or more of the second devices 120, to transcribe the communication session, and provide indications regarding one or more questions that may be determined to be asked during the communication session.

The first device 110 may send a request for a communication session to the communication routing system 140. The communication routing system 140 may obtain the request from the first device 110. In some embodiments, the request may include an identifier of the first device 110.

Using the identifier of the first device 110, the communication routing system 140 may obtain profile data regarding the first user associated with the first device 110. The profile data may include information about the first user, such as demographic information, including name, age, sex, address, etc., among other demographic data. In some embodiments, the profile data may further include health related information about the first user. For example, the health related information may include the height, weight, medical allergies, previous medical procedures, amount of time since previous medical procedures, and current medical conditions, etc., among other health related information. In some embodiments, the profile data may include transcriptions of conversations between the first user and the second users.

Using the profile data and/or other information about the first user, such as medical data about the first user, the communication routing system 140 may select one or more of the second devices 120 for the communication session with the first device 110. After selecting one or more of the second devices 120, the communication routing system 140 may establish the communication session. Alternatively or additionally, the communication routing system 140 may select one or more of the second devices 120 for the communication session with the first device 110 based on one or more of the second devices 120 being identified in the request from the first device 110.

During a communication session, the communication routing system 140 may be configured to receive media data from the first device 110 and the selected one or more of the second devices 120. The communication routing system 140 may route the media data to the transcription system 160 for generation of transcript data. The transcription system 160 may generate transcript data. The transcript data may also be transmitted to the first device 110 and the selected one or more of the second devices 120 for presentation by the first device 110 and the selected one or more of the second devices 120.

Further explanation of the transcription process and routing is now described. However, it is described in the context of a communication session between the first device 110 and the first second-device 120*a* for ease of explanation.

As mentioned, the first device 110 and the first second-device 120*a* may exchange media data during a communication session. In some embodiments, the media data may include video and/or audio data. For example, the first device 110 may send first audio data and first video data to the first second-device 120*a* and the first second-device 120*a* may send second audio data and second video data to the first device 110. Alternatively or additionally, the media data may include audio data but not video data.

During the communication session, the media data exchanged between the first device 110 and the first second-device 120*a* may be routed through the communication routing system 140. During the routing of the media data between the first device 110 and the first second-device 120*a*, the communication routing system 140 may be configured to duplicate the audio data from the media data and provide the duplicated audio data to the transcription system 160.

The transcription system 160 may receive the duplicated first audio. The transcription system 160 may generate the first transcript data of the duplicated first audio. The first transcript data may include a transcription of the duplicated first audio.

In some embodiments, the transcription system 160 may generate the first transcript data using a machine transcription of the duplicated first audio. In some embodiments, before a machine transcription is made of the duplicated first audio, the duplicated first audio may be listened to and re-voiced by another person. In these and other embodiments, the other person may make corrections to the machine transcription.

The transcription system 160 may provide the first transcript data to the communication routing system 140. The communication routing system 140 may route the first transcript data to the first second-device 120*a*. The first second-device 120*a* may present the first transcript data to a user of the first second-device 120*a* on a display of the first second-device 120*a*. In these or other embodiments, the communication routing system 140 may route the first transcript data to the question system 170. Additionally or alternatively, the first transcript data may be provided to the question system 170 via some other communication scheme that may not include the communication routing system 140.

The communication routing system 140 and the transcription system 160 may handle the second media data from the first second-device 120*a* in an analogous manner. For example, the communication routing system 140 may generate duplicated second audio of second audio of the second media data and the transcription system 160 may generate second transcript data based on the duplicated second audio. The second transcript data may be provided to the first device 110 for presentation of the first user of the first device 110. Additionally or alternatively, the second transcript data may be provided to the question system 170.

In some embodiments, the generation and delivery of the transcript data of the first and second media may both be in substantially real-time or real-time. In these and other embodiments, the first device 110 may present the second transcript data concurrently with the second media data in substantially real-time or real-time. Concurrent presentation of the second transcript data and the second media data in substantially real-time may indicate that when audio is presented, a transcription that corresponds to the presented audio is also presented with a delay of less than 1, 2, 5, 10, or 15 seconds between the transcription and the audio. Alternatively or additionally, the generation and delivery of transcript data of one of the first and second media may be in substantially real-time or real-time and the generation and/or delivery of transcript data of another of the first and second media may not be in real time.

In some embodiments, the first transcript data and the second transcript data may be combined by interweaving data segments of the first transcript data and the second transcript data. In these and other embodiments, first data segments of the first transcript data and second data segments of the second transcript data may be interweaved such that the first data segments and the second data segments are combined in substantially chronological order. In some embodiments, the transcription system 160 may perform the interweaving. In these or other embodiments, the question system 170 may perform the interweaving.

In some embodiments, when a third device, such as the second second-device 120*b* participates in a communication session between the first device 110 and the first second-device 120*a*, third transcript data may be generated for third audio generated by the third device. In these and other embodiments, the third transcript data may be provided to the first device 110 and/or the first second-device 120*a* and the third device may receive the first and/or second transcript data from the first device 110 and the first second-device 120*a*, respectively. In these or other embodiments, the third transcript data may be combined by interweaving third data segments of the third transcript data with the first and second data segments. In some embodiments, the transcription system 160 may perform the interweaving. In these or other embodiments, the question system 170 may perform the interweaving In some embodiments, the question system 170 may be configured to perform one or more operations related to the displaying of questions on the first device 110 and/or one or more of the second devices 120 during the communication session. In these or other embodiments, the question system 170 may obtain one or more questions that may be determined to be asked during the communication session.

In some embodiments, the one or more questions may be based on a topic of the communication session. For example, the communication session type may be a patient and a healthcare professional communication type session. In these or other embodiments, the questions may include those that may generally apply to a person's medical condition or general wellbeing (e.g., height, weight, sleep patterns, blood pressure, medications being taken, supplements being taken, etc.). Additionally or alternatively, the patient may have a specific reason for contacting the healthcare professional and the questions may include those that may apply to the specific reason for the communication session. For example, in some embodiments, the patient may initiate the communication session for a particular type of injury or health condition. The questions may thus include questions about other symptoms or things to look for that may be associated with the injury or health condition. In these or other embodiments, the questions may include questions about other injuries or health conditions that may be related to or mistaken with the identified injury or health condition.

In these or other embodiments, one or more of the questions may be based on profile data of one or more participants in the communication session. For example, in some embodiments, with respect to a healthcare professional/patient communication session, one or more questions may be based on the profile data of the first user (e.g., the patient) such as discussed above. In these or other embodiments, one or more of the questions may be specifically formulated according to the information included in the profile data.

Additionally or alternatively, one or more of the questions may be based on profile data of the healthcare professional that may include credentials, an expertise level, a specialty, education, etc. of the healthcare professional. For instance, one or more of the questions may be those that may typically be asked with respect to a particular specialty or expertise level of the healthcare professional.

In these or other embodiments, the questions may include questions that may be required to be asked according to a policy. For example, in some instances a policy related to a healthcare professional/patient interaction may include one or more questions that are mandated to be asked of the patient. In some embodiments, the questions may include the mandated questions.

In these or other embodiments, the questions may include one or more follow-up questions that may be based on the answers to one or more previously asked questions. For example, a previously asked question may relate to what medications the patient is taking. A follow-up question may relate to asking about dosage information, refill information, prescribing doctor information, issuing pharmacy information, prescription date, amount of doses remaining, possible contraindications, etc.

In some embodiments, the question system 170 may be configured to obtain one or more of the questions by receiving the questions. For example, the question system 170 may receive one or more of the questions as user input in some embodiments. Additionally or alternatively, the question system 170 may receive one or more questions from another system, apparatus, device, or program that may have previously determined or obtained the received questions. For example, in some embodiments, the questions may be included in a pre-defined library of questions that may be stored in a database. In these or other embodiments, the question system 170 may be configured to access the database to obtain the pre-defined library of questions.

In these or other embodiments, the question system 170 may be configured to obtain one or more questions by determining the questions. For example, in some embodiments, the question system 170 may be configured to perform topic analysis operations with respect to the transcript data to identify subject matter of the communication session. Based on the topic analysis, the question system 170 may be configured to generate one or more of the questions that correspond to the identified subject matter.

As another example, in some embodiments, the question system 170 may be configured to identify participants in the communication session (e.g., based on user input, identifiers associated with the user devices, an analysis of the transcript data, etc.). The question system 170 may be configured to acquire information about the identified participants and to generate one or more questions based on the acquired information. For example, the question system 170 may be configured to acquire information from the profile data of the first user and may generate one or more questions based on the information acquired from the profile data of the first user. In these or other embodiments, the question system 170 may determine the questions in real-time as the communication session is occurring.

In these or other embodiments, the question system 170 may be configured to generate one or more follow-up questions based on the transcript data. For example, as described previously, the first transcript data may include a transcript of first audio data from the first device and the second transcript data may include a transcript of second audio data from the second device. Thus, the first transcript data may include a transcript of words spoken by the first user during the communication session and the second transcript data may include a transcript of words spoken by the second user during the communication session. Thus, there may be no or little uncertainty regarding what is said by the first user and what is said by the second user. As such, in some embodiments, using the first transcript data and the second transcript data, the question system 170 may identify when a particular question is asked and an answer to the particular question.

For example, as discussed further below, based on an analysis of the second transcript data, the question system 170 may identify that the particular question has been asked. Further, based on the interweaving of data segments of the second transcript data with those of the first transcript data, the question system 170 may be configured to determine that first data segments of the first transcript data that follow second data segments of the second transcript data that correspond to the question may correspond to an answer to the question. The question system 170 may identify information in the answer to determine one or more follow-up questions. In some embodiments, the question system 170 may determine the follow-up questions based on machine-learning. In these or other embodiments, the question system 170 may determine the follow-up questions in real-time as the communication session is occurring.

In some embodiments, the question system 170 may cause the presentation of the determined questions on the first device 110 and/or one or more of the second devices 120. For the ease of explanation, the presentation of questions is given in the context of a particular communication session conducted by the first device 110 and the first second device 102*a*.

By way of example, the first user of the first device 110 participating in the particular communication session may be a patient and the second user of the first second device 120*a* participating in the particular communication system may be a healthcare professional. The question system 170 may be configured to obtain one or more questions that may be asked by the second user during the particular communication session. The obtained questions may relate to a health condition of the first user, general wellbeing of the first user, a purpose of initiating the communication session by the first user, etc.

In some embodiments, the question system 170 may be configured to generate question data that may include the obtained questions. In these or other embodiments, the question system 170 may also be configured to communicate the question data to the first second device 120*a*. The question data may include instructions for the first second device 120*a* to present the corresponding questions such that the first second device 120*a* may remind the second user to ask the questions during the communication session. In some embodiments, the question data may be included in the transcript data that may be communicated to the first second device 120*a*. In these or other embodiments, the question data may be communicated at a beginning of the communication session such that one or more of the questions may be presented to the second user at the beginning of and/or during the communication session. Additionally or alternatively, the question system 170 may not initially communicate the question data to the first second device 120*a*. In these or other embodiments, as discussed above, in some instances the questions may include one or more follow-up questions. In some embodiments, the follow-up questions may be included in follow-up question data that may be generated and communicated to the first second device 120*a* after generation of previous question data. In these or other embodiments, the follow-up question data may be communicated in real-time in conjunction with the determination of the follow-up questions.

The question system 170 may be configured to determine which of the obtained questions have been asked in the communication session. In some embodiments, the question system 170 may be configured to make the determination during the communication session. The question system 170 may be configured to determine which questions have been asked based on an analysis of the transcript data in some embodiments.

For example, the questions may be determined as to be asked by the second user of the first second device 120*a*. The question system 170 may thus be configured to analyze the second transcript data based on the second transcript data deriving from the first second device 120*a*. The analyzing of the second transcript data may include searching for word combinations that may be included in or correspond to the obtained questions. In some embodiments, the question system 170 may be configured to insert question tags in transcript data segments of the transcript data (e.g., transcript data segments of the second transcript data) that include those questions that are determined as being asked. Transcript data segments that include questions that are determined as being asked may be referred to as "question data segments" in the present disclosure. The tagging of a particular question data segment may thus indicate that the particular question data segment includes a particular question that corresponds to the question tag.

In some embodiments, the transcript data may be stored as part of a record of the particular communication session. In these or other embodiments, the tagging of the question data segments may be used to indicate where in the corresponding transcription the questions were asked. For example, in some embodiments, the record may include at the top of the transcription a list of questions that were asked during the particular communication session. Additionally, the transcript data may include links from the listed questions to the corresponding question data segments in which the links use the question tags to identify the corresponding question data segments. As such, the tagging of the question data segments may allow for a more efficient review of the transcription.

In these or other embodiments, the question system 170 may communicate to the first second device 120*a* that a particular question has been asked such that the first second device 120*a* may present an indication that the particular question has been asked. By way of example, the indication may include crossing out the particular question, emphasizing the particular question, checking a box next to the particular question, removing the particular question from being presented, changing a font, format, etc. of the particular question, or any other suitable indication. In some embodiments, the question system 170 may communicate updated question data with the tagging of the particular question as being asked. In these and other embodiments, the first second device 120*a* may present the indication with respect to the particular question based on the tagging of the particular question in the question data.

In these or other embodiments, the question system 170 may be configured to communicate to the first second device 120*a* that a particular question has not been asked such that the first second device 120*a* may present an indication that the particular question has not been asked. By way of example, the indication may include presenting the particular question on the first second device 120*a*, emphasizing the particular question, emphasizing a box next to the particular question, changing a font, format, etc. of the particular question, or any other suitable indication. In some embodiments, the question system 170 may communicate updated question data with the tagging of the particular question as not being asked and the first second device 120*a* may present the indication with respect to the particular question based on the tagging of the particular question in the question data.

In the present disclosure, an indication of questions as being asked may also indicate which questions have not been asked and an indication of questions that have not been asked may similarly indicate which questions have been asked. For example, presentation of all of the questions in which the questions that have been asked are indicated with some sort of differentiating characteristic as compared to the questions that have not been asked thus provides an indication as to which questions have not been asked. In some embodiments, the indications may be updated in real-time during the communication session as the corresponding questions are determined as being asked or not yet asked.

In some embodiments, the question system 170 may determine which questions have not been asked based on the analysis of the transcript data not finding word combinations that correspond to the unasked questions. In these or other embodiments, the question system 170 may determine which questions have not been asked based on which questions have not been tagged as being asked.

In these or other embodiments, the question system 170 may be configured to direct the first second device 120*a* to present reminders to ask one or more questions that have been determined to not have been asked. In some embodiments, the direction may include a control signal or may be included in question data that may be communicated to the first second device 120*a*. For example, updated question data with tagging of questions that have not been asked may be communicated along with directions to provide a reminder with respect to questions that have not been asked.

In some embodiments, the presentation of a particular reminder with respect to a particular question may include emphasizing the particular question, causing the particular question to be presented (e.g., displayed) on the first second device 120*a*, presenting words that state that the particular question has not been asked, or any other suitable reminder. The presentation of the particular question may be a subsequent presentation after one or more previous presentations or may be an initial presentation of the particular question.

In some embodiments, the question system 170 may be configured to cause the presentation of reminders in response to an event. In some embodiments, the event may be after a particular amount of time has passed since initiation of the communication session (e.g., after 1-5 minutes). In these or other embodiments, the event may be after a particular amount of time has passed since a presentation of a particular question or a previous reminder of the particular question.

Additionally or alternatively, the event may be an indication that the communication session may terminate soon. For example, in some embodiments, the question system 170 may be configured to identify in the transcript data words or phrases that are commonly associated with the ending of a communication session. In response to identification of such words or phrases, the question system 170 may determine that the communication session may soon terminate and may cause the presentation of a reminder in response to the determination. As another example, the question system 170 may be configured to identify that an indication to end the communication session (e.g., an end call command, hanging up of the first device 110 or one of the second devices 120) has been initiated. Prior to the communication session ending or allowing the communication session to end (e.g., through a communication with the communication routing system 140), the question system 170 may be configured to cause presentation of the reminder.

In some instances, a question may be asked during a communication session, but the question may not be answered. In the present disclosure, reference to a question not being answered may include questions that are completely unanswered (e.g., ignored questions) or questions that are partially answered. Additionally, questions that have been determined as not having been answered may be referred to as "unanswered questions" in the present disclosure.

In some embodiments, the question system 170 may be configured to determine which of the asked questions have been answered. In these or other embodiments, the question system 170 may be configured to make the determination during the communication session. The question system 170 may be configured to determine which questions have been answered based on an analysis of the transcript data in some embodiments.

For example, the question system 170 may be configured to analyze the first transcript data based on the first transcript data deriving from the first device 110 and based on the questions as being determined to be asked by the second user and directed toward the first user. The analyzing of the first transcript data may include analyzing data segments of the first transcript data that chronologically follow question data segments of the second transcript data. For example, particular first transcript data segments of the first transcript data that chronologically occur immediately after or within a particular amount of time after a particular question data segment of the second transcript may be analyzed. The analysis may be done to determine whether the particular first transcript data segments include words or word combinations that may commonly be associated with answers to the particular question. In response to the particular first transcript data segments including words or combinations, the question system 170 may be configured to determine that the particular question has been answered.

In some embodiments, the question system 170 may be configured to insert answer tags in transcript data segments of the transcript data (e.g., the particular first transcript data segments) that include answers to questions. Transcript data segments that include answers to questions that are determined as being asked may be referred to as "answer data segments" in the present disclosure. The tagging of a particular answer data segment may thus indicate that the particular answer data segment includes an answer to a particular question.

As mentioned above, in some embodiments, the transcript data may be stored as part of a record of the particular communication session. In these or other embodiments, the tagging of the answer data segments may be used to indicate where in the corresponding transcription the questions were answered. Additionally or alternatively, in some embodiments, a particular answer tag that corresponds to a particular answer data segment may be included in a particular question data segment that corresponds to a particular question in which the particular answer data segment may correspond to an answer to the particular question. In these or other embodiments, a particular question tag that corresponds to the particular question data segment may be included in the particular answer data segment. Therefore, in some embodiments, the questions and corresponding answers may be cross-referenced in the transcript data, which may allow for a more efficient review of the corresponding transcription.

Additionally or alternatively, in some embodiments, the record may include at a beginning of the transcription a list of questions that were asked during the particular communication session. In these or other embodiments, the transcript data may include links from the listed questions to the corresponding answer data segments in which the links use the answer tags to identify the corresponding answer data segments. As such, the tagging of the answer data segments may allow for a more efficient review of the corresponding transcription.

In these or other embodiments, the question system 170 may communicate to the first second device 120*a* that a particular question has been answered such that the first second device 120*a* may present an indication that the particular question has been answered. By way of example, the indication may include any suitable indication including those discussed above. In some embodiments, the question system 170 may communicate updated question data with the tagging of the particular question as being answered and the first second device 120*a* may present the indication with respect to the particular question based on the tagging of the particular question in the question data.

In these or other embodiments, the question system 170 may be configured to communicate to the first second device 120*a* that a particular question has not been answered such that the first second device 120*a* may present an indication that the particular question has not been answered. By way of example, the indication may include presenting the particular question on the first second device 120*a*, emphasizing the particular question, emphasizing a box next to the particular question, changing a font, format, etc. of the particular question, or any other suitable indication. In some embodiments, the question system 170 may communicate updated question data with the tagging of the particular question as not being answered and the first second device 120*a* may present the indication with respect to the particular question based on the tagging of the particular question in the question data.

In the present disclosure, an indication of questions as being answered may also indicate which questions have not been answered and an indication of questions that have not been answered may similarly indicate which questions have been answered. For example, presentation of all of the questions in which the questions that have been answered are indicated with some sort of differentiating characteristic as compared to the questions that have not been answered thus provides an indication as to which questions have not been answered. In some embodiments, the indications may be updated in real-time during the communication session as the corresponding questions are determined as being answered.

In some embodiments, the question system 170 may determine which questions have not been answered based on the analysis of the transcript data not finding word combinations that correspond to answers of asked questions. In these or other embodiments, the question system 170 may determine which questions have not been answered based on which questions have not been tagged as being answered.

In these or other embodiments, the question system 170 may be configured to direct the first second device 120*a* to present reminders to re-ask one or more questions that have been determined not to have been answered. In some embodiments, the direction may include a control signal or may be included in question data that may be communicated to the first second device 120*a*. For example, updated question data with tagging of questions that have not yet been answered may be communicated along with directions to provide a reminder with respect to questions that have not been answered.

In some embodiments, the presentation of a particular reminder with respect to a particular question may include emphasizing the particular question, causing the particular question to be presented (e.g., displayed) on the first second device 120*a*, presenting words that state that the particular question has not been answered, or any other suitable reminder. In some embodiments, the question system 170 may be configured to cause the presentation of reminders that one or more questions have not been answered in response to an event, such as the events described above.

In some embodiments, the question system 170 may be configured to maintain the communication session until after it has been determined that the questions were all asked and/or answered. For example, in some embodiments, the question system 170 may be configured to direct the communication routing system 140, the first device 110, and/or the first second device 120*a* to not close or end the communication session if it has been determined that one or more question have not been asked and/or answered.

In these or other embodiments, in response to determining that the communication session may end soon and in response to determining that one or more questions have not been asked and/or answered, the question system 170 may be configured to cause that a prompt be presented by the first second device 120*a*. The prompt may ask the whether or not the communication session may be ended despite one or more questions not being asked and/or answered. In some embodiments, the prompt may include which questions have not been asked and/or answered. In these or other embodiments, the communication session may close or end in response to a response to the prompt that indicates that the communication session may close even if one or more questions have not been asked and/or answered.

Modifications, additions, or omissions may be made to the environment 100 without departing from the scope of the present disclosure. For example, in some embodiments, the transcription system 160 may be part of the question system 170. In these or other embodiments, the transcription system 160 and/or the question system 170 may be part of the communication routing system 140. Additionally or alternatively, in some embodiments, the communication routing system 140 may be omitted. In these or other embodiments, selection of a second device 120 may be simplified and may be based on a contact number or other identifier (e.g., a telephone number, a username, etc.) selected at the first device 110 and used by the first device 110 to establish the communication session.

Moreover, in some embodiments, the routing of the audio with respect to the transcription system 160 may vary from as described in the present disclosure. Additionally or alternatively, the operations described as being performed by a particular system may vary in some instances. For example, in some embodiments, one or more operations described as being performed by the question system 170 may be performed at the first device 110 and/or the second devices 120 based on transcript data received at the first device 110 and/or the second devices 120.

Moreover, although certain examples have been described in the context of communication sessions between healthcare professionals and patients, the present disclosure is not limited to such circumstances and such an example is used to help provide an understanding of the present disclosure. As such, the principles outlined in the present disclosure may apply to any applicable communication session where reminders regarding the asking and/or answering of questions may be used. For example, the principles and teachings described in the present disclosure may be applicable to customer service communication sessions, sales communication sessions, attorney/client communication sessions, employer/employee communication sessions, supervisor/supervisee communication sessions, or any other applicable communication session where asking of certain questions may be used.

Figure 2:
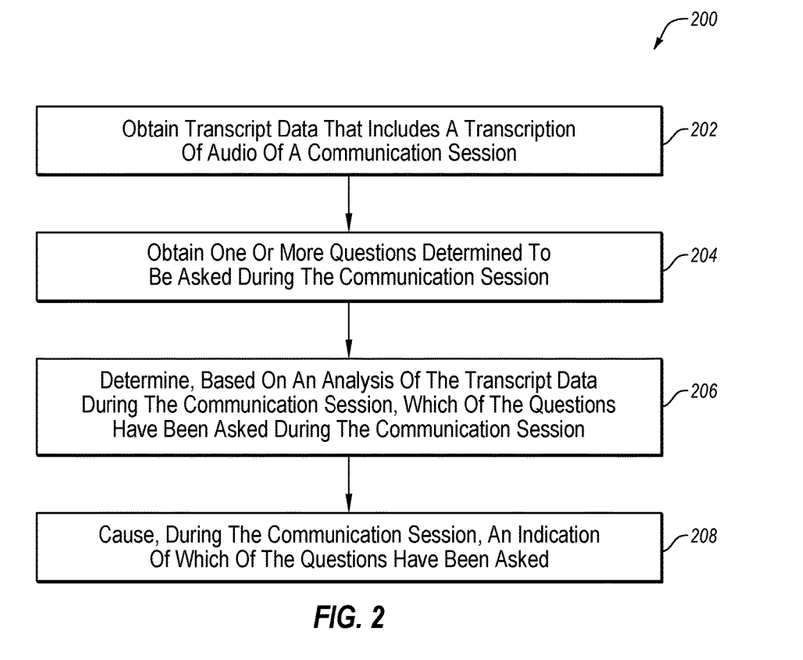
FIG. 2 is a flowchart of an example method of providing indications with respect to questions of a communication session.

FIG. 2 is a flowchart of an example method 200 of providing indications with respect to questions of a communication session. The method 200 may be arranged in accordance with at least one embodiment described in the present disclosure. The method 200 may be performed, in whole or in part, in some embodiments by a system or combinations of components in a system or environment as described in the present disclosure. For example, the method 200 may be performed, in whole or in part, by one or more elements of the environment 100 and/or the system 300 of FIGS. 1 and 3, respectively. In these and other embodiments, some or all of the operations of the method 200 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 200 may begin at block 202, where transcript data that includes a transcription of audio of a communication session may be obtained. In some embodiments, the obtaining of the transcript data may include generating the transcript data. In these or other embodiments, the obtaining of the transcript data may include receiving the transcript data. The transcript data described above with respect to FIG. 1 may be an example of the transcript data that is generated. Additionally or alternatively, in some embodiments, the audio may include first device audio sent from a first device to a second device during the communication session. In these or other embodiments, the audio may include second device audio sent from the second device to the first device during the communication session.

At block 204, one or more questions that have been determined to be asked during the communication session may be obtained. The questions may be obtained as discussed above with respect to FIG. 1. For example, in some embodiments, the questions may be determined based on one or more of: a topic of the communication session, a profile of a first user of the first device, and a profile of as second user of the second device in some embodiments.

At block 206, it may be determined as to which of the questions have been asked during the communication session. In some embodiments, the determination may be made such as described above with respect to FIG. 1. For example, in some embodiments, the transcript data may be analyzed to determine which questions have been asked. The determination may include determining that a particular question has not been asked or determining that a particular question has been asked. In these or other embodiments, the method 200 may include tagging the questions that have been determined as being asked and determining that a particular question has not been asked based on the particular question not being tagged. Additionally or alternatively, one or more questions that have been determined as not been asked may be tagged as such.

At block 210, an indication as to which of the questions have been asked may be caused to be presented on a device that is involved in the communication session. For example, the indication may be caused to be presented on the first device and/or the second device. The indication may be any suitable indication such as described above with respect to FIG. 1. Additionally or alternatively, in some embodiments, the method 200 may include determining an event such as described above (e.g., passage of a certain amount of time, that the communication session is about to terminate) and causing presentation of the indication in response to the event.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 200 may include one or more operations related to establishing the communication session between the first device and the second device such that the first device audio is sent from the first device to the second device and such that the second device audio is sent from the second device to the first device during the communication session. In these or other embodiments, the method 200 may include one or more operations related to receiving the first device audio as the first device audio is routed to the second device and/or receiving the second device audio as the second device audio is routed to the first device.

Additionally or alternatively, in some embodiments, the method 200 may include one or more operations related to causing, during the communication session, the presentation of a reminder that a particular question has not been asked and/or a reminder to ask a particular question of the plurality of questions in response to determining that the particular question has not been asked. In these or other embodiments, the operations of block 210 may be omitted and replaced with the presentation of a reminder. Additionally or alternatively, the presentation of the reminder may be in addition to the operations at block 210.

In these or other embodiments, the method 200 may include one or more operations related to determining, based on an analysis of the transcript data during the communication session, which of the plurality of questions have been answered during the communication session; and causing, during the communication session, the second device to indicate which of the plurality of questions have been answered. Additionally or alternatively, the method 200 may include one or more operations related to determining, based on the analysis of the transcript data, that a particular question has not been answered during the communication session and causing, during the communication session, the presentation of an indication that the particular question has not been answered in response to determining that the particular question has not been answered during the communication session.

In these or other embodiments, the method 200 may include one or more operations related to identifying a question data segment of the transcript data that includes a particular question of the questions and inserting, in the question data segment, a question tag that indicates that the question data segment includes the particular question. Additionally or alternatively, the method 200 may include one or more operations related to identifying an answer data segment of the transcript data that includes an answer to the particular question and inserting, in the answer data segment, an answer tag that indicates that the answer data segment includes the answer to the particular question. In these or other embodiments, the method 200 may include one or more operations related to linking the question data segment and the answer data segment in response to both the question data segment and the answer data segment corresponding to the particular question.

Figure 3:
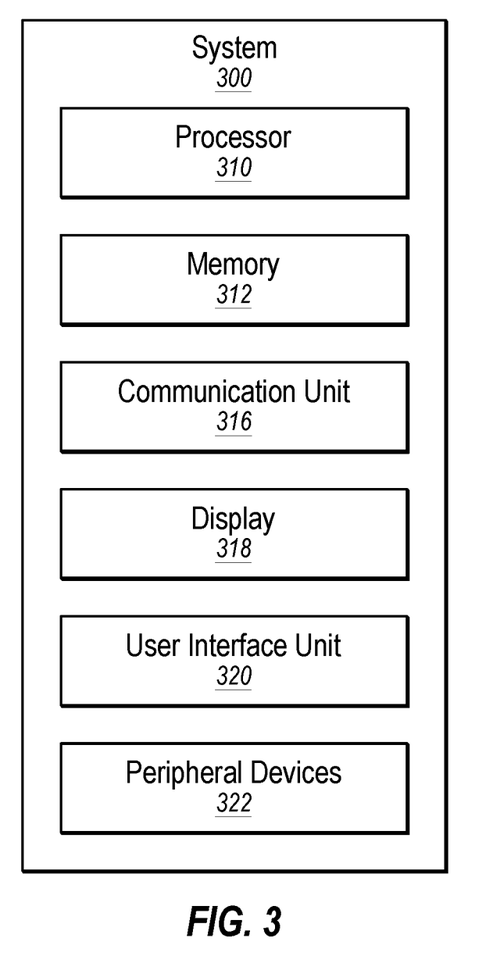
FIG. 3 illustrates an example computing system that may be used to provide indications with respect to questions of a communication session, all arranged according to one or more embodiments described in the present disclosure.

FIG. 3 illustrates an example computing system 300 that may be used to provide indications with respect to questions of a communication session. The system 300 may be arranged in accordance with at least one embodiment described in the present disclosure. The system 300 may include a processor 310, memory 312, a communication unit 316, a display 318, a user interface unit 320, and a peripheral device 322, which all may be communicatively coupled. In some embodiments, the system 300 may be part of any of the systems or devices described in this disclosure.

For example, the system 300 may be part of the first device 110 of FIG. 1 and may be configured to perform one or more of the tasks described above with respect to the first device 110. As another example, the system 300 may be part of the second devices 120 of FIG. 1 and may be configured to perform one or more of the tasks described above with respect to the second devices 120. As another example, the system 300 may be part of the transcription system 160 of FIG. 1 and may be configured to perform one or more of the tasks described above with respect to the transcription system 160. As another example, the system 300 may be part of the communication routing system 140 of FIG. 1 and may be configured to perform one or more of the tasks described above with respect to the communication routing system 140. As another example, the system 300 may be part of the question system 170 of FIG. 1 and may be configured to perform one or more of the tasks described above with respect to the question system 170.

Generally, the processor 310 may include any suitable special-purpose or general-purpose computer, computing entity, or processing device including various computer hardware or software modules and may be configured to execute instructions stored on any applicable computer-readable storage media. For example, the processor 310 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

Although illustrated as a single processor in FIG. 3, it is understood that the processor 310 may include any number of processors distributed across any number of networks or physical locations that are configured to perform individually or collectively any number of operations described herein. In some embodiments, the processor 310 may interpret and/or execute program instructions and/or process data stored in the memory 312. In some embodiments, the processor 310 may execute the program instructions stored in the memory 312.

For example, in some embodiments, processor 310 may execute program instructions stored in the memory 312 that are related to providing indications with respect to questions of a communication session such that the system 300 may perform or direct the performance of the operations associated therewith as directed by the instructions. In these and other embodiments, instructions may be used to perform one or more operations of the method 200 of FIG. 2.

The memory 312 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 310. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 310 to perform a certain operation or group of operations as described in this disclosure. In these and other embodiments, the term "non-transitory" as explained in the present disclosure should be construed to exclude only those types of transitory media that were found to fall outside the scope of patentable subject matter in the Federal Circuit decision of *In re Nuijten,* 500 F.3d 1346 (Fed. Cir. 2007). Combinations of the above may also be included within the scope of computer-readable media.

The communication unit 316 may include any component, device, system, or combination thereof that is configured to transmit or receive information over a network. In some embodiments, the communication unit 316 may communicate with other devices at other locations, the same location, or even other components within the same system. For example, the communication unit 316 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, cellular communication facilities, etc.), and/or the like. The communication unit 316 may permit data to be exchanged with a network and/or any other devices or systems described in the present disclosure. For example, when the system 300 is included in the first device 110 of FIG. 1, the communication unit 316 may allow the first device 110 to communicate with the communication routing system 140.

The display 318 may be configured as one or more displays, like an LCD, LED, or other type of display. The display 318 may be configured to present video, text captions, user interfaces, and other data as directed by the processor 310. For example, when the system 300 is included in the first device 110 of FIG. 1, the display 318 may be configured to present second video from a second device, a transcript of second audio from the second device, and/or indications of questions and/or answers related to a corresponding communication session. As another example, when the system 300 is included in the second devices 120 of FIG. 1, the display 318 may be configured to present first video from a first device, a transcript of first audio from the first device, and/or indications of questions and/or answers related to a corresponding communication session.

The user interface unit 320 may include any device to allow a user to interface with the system 300. For example, the user interface unit 320 may include a mouse, a track pad, a keyboard, buttons, and/or a touchscreen, among other devices. The user interface unit 320 may receive input from a user and provide the input to the processor 310.

The peripheral devices 322 may include one or more devices. For example, the peripheral devices may include a microphone, an imager, and/or a speaker, among other peripheral devices. In these and other embodiments, the microphone may be configured to capture audio. The imager may be configured to capture digital images. The digital images may be captured in a manner to produce video or image data. In some embodiments, the speaker may broadcast audio received by the system 300 or otherwise generated by the system 300. Modifications, additions, or omissions may be made to the system 300 without departing from the scope of the present disclosure. For example, the system 300 may not include one or more of: the display 318, the user interface unit 320, and peripheral device 322.

Modifications, additions, or omissions may be made to the system 300 without departing from the scope of the present disclosure. For example, in some embodiments, the system 300 may include any number of other components that may not be explicitly illustrated or described. Further, depending on certain implementations, the system 300 may not include one or more of the components illustrated and described.

In some embodiments, the different components, modules, engines, and services described herein may be implemented as objects or processes that execute on a computing system (e.g., as separate threads). While some of the systems and methods described herein are generally described as being implemented in software (stored on and/or executed by general purpose hardware), specific hardware implementations or a combination of software and specific hardware implementations are also possible and contemplated.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A computer-implemented method to provide indications with respect to questions of a communication, the method comprising:

obtaining transcript data that includes a transcription of audio of a communication session;

obtaining a plurality of questions determined to be asked during the communication session;

determining, based on an analysis of the transcript data during the communication session, that a particular question of the plurality of questions has not been asked during the communication session; and causing, during the communication session, a device involved in the communication session to present a reminder to ask the particular question in response to determining that the particular question has not been asked.

2. The method of claim 1, further comprising determining the plurality of questions based on one or more of: a topic of the communication session, a profile of a first participant of the communication session, and a profile of a second participant of the communication session.

3. The method of claim 1, further comprising:
determining that the communication session is about to terminate; and
causing, during the communication session, the device to display the reminder to ask the particular question in response to determining that the communication session is about to terminate.

4. The method of claim 1, further comprising:
determining, during the communication session based on the analysis of the transcript data, which of the plurality of questions have been asked during the communication session;
tagging the questions that have been determined as being asked; and
determining that the particular question of the plurality of questions has not been asked during the communication session based on the particular question not being tagged.

5. The method of claim 4, further comprising causing the device to indicate which of the plurality of questions have been asked.

6. The method of claim 1, further comprising:
determining, based on the analysis of the transcript data, that the particular question has not been answered during the communication session; and
causing, during the communication session, the device to present an indication that the particular question has not been answered in response to determining that the particular question has not been answered during the communication session.

7. The method of claim 1, further comprising:
identifying a question data segment of the transcript data that includes the particular question; and
inserting, in the question data segment, a question tag that indicates that the question data segment includes the particular question.

8. The method of claim 7, further comprising:
identifying an answer data segment of the transcript data that includes an answer to the particular question; and
inserting, in the answer data segment, an answer tag that indicates that the answer data segment includes the answer to the particular question.

9. The method of claim 8, further comprising linking the question data segment and the answer data segment in response to both the question data segment and the answer data segment corresponding to the particular question.

10. One or more non-transitory computer-readable media configured to store instructions that, in response to being executed by one or more processors, cause one or more systems to perform the method of claim 1.

11. A system comprising:
one or more processors; and
one or more computer-readable media configured to store instructions that in response to being executed by the one or more processors cause the system to perform operations, the operations comprising:
obtaining transcript data that includes a transcription of audio of a communication session;
obtaining a plurality of questions determined to be asked during the communication session;
determining, based on an analysis of the transcript data during the communication session, which of the plurality of questions have been asked during the communication session; and
causing, during the communication session, a device involved in the communication session to indicate which of the plurality of questions have been asked.

12. The system of claim 11, wherein the operations further comprise causing, during the communication session, the device to present a reminder to ask a particular question of the plurality of questions in response to determining that the particular question has not been asked.

13. The system of claim 12, wherein the operations further comprise:
determining that the communication session is about to terminate; and
causing the device to present the reminder to ask the particular question in response to determining that the communication session is about to terminate.

14. The system of claim 11, wherein the operations further comprise:
determining, based on the analysis of the transcript data, that a particular question of the plurality of questions has not been answered during the communication session; and
causing, during the communication session, the device to present an indication that the particular question has not been answered in response to determining that the particular question has not been answered during the communication session.

15. The system of claim 11, wherein the operations further comprise:
identifying a question data segment of the transcript data that includes a particular question of the plurality of questions; and
inserting, in the question data segment, a question tag that indicates that the question data segment includes the particular question.

16. The system of claim 11, wherein the operations further comprise:
identifying an answer data segment of the transcript data that includes an answer to a particular question of the plurality of questions; and
inserting, in the answer data segment, an answer tag that indicates that the answer data segment includes the answer to the particular question.

17. The system of claim 11, wherein the operations further comprise:
determining, based on the analysis of the transcript data during the communication session, which of the plurality of questions have been answered during the communication session; and
causing, during the communication session, the device to indicate which of the plurality of questions have been answered.

18. A computer-implemented method to provide indications with respect to questions of a communication, the method comprising:
obtaining transcript data that includes a transcription of audio of a communication session;
obtaining a plurality of questions determined to be asked during the communication session;

determining, based on an analysis of the transcript data during the communication session, which of the plurality of questions have been asked during the communication session; and causing, during the communication session, a device involved in the communication session to indicate which of the plurality of questions have been asked.

19. The method of claim 18, further comprising:

determining, based on the analysis of the transcript data during the communication session, which of the plurality of questions have been answered during the communication session; and causing, during the communication session, the device to indicate which of the plurality of questions have been answered.

20. One or more non-transitory computer-readable media configured to store instructions that, in response to being executed by one or more processors, cause one or more systems to perform the method of claim 18.

* * * * *